United States Patent
Butler et al.

(10) Patent No.: US 6,967,218 B2
(45) Date of Patent: Nov. 22, 2005

(54) PRAVASTATIN PHARMACEUTICAL FORMULATIONS AND METHODS OF THEIR USE

(75) Inventors: Jackie Butler, Westmeath (IR); John Devane, Roscommon (IR); Paul Stark, Westmeath (IR)

(73) Assignee: Biovail Laboratories, Inc., St. Michael, Barbados (KN)

( * ) Notice: Subject to any disclaimer, the term of this patent is extended or adjusted under 35 U.S.C. 154(b) by 0 days.

(21) Appl. No.: 10/339,487

(22) Filed: Jan. 10, 2003

(65) Prior Publication Data

US 2003/0176502 A1 Sep. 18, 2003

Related U.S. Application Data

(60) Provisional application No. 60/347,775, filed on Jan. 11, 2002, and provisional application No. 60/407,269, filed on Sep. 3, 2002.

(51) Int. Cl.[7] ...................... A61K 31/21; A61K 31/225
(52) U.S. Cl. ........................................ 514/510; 514/548
(58) Field of Search ................................ 424/408, 464, 424/465, 468, 474; 514/548, 510, 310, 307, 299, 279, 277, 568

(56) References Cited

U.S. PATENT DOCUMENTS 4,997,658 A * 3/1991 Alberts et al. .............. 424/473
5,916,595 A 6/1999 Chou et al.
6,331,316 B1 12/2001 Ullah et al.
2003/0091630 A1 * 5/2003 Louis-Helm et al. ....... 424/468

FOREIGN PATENT DOCUMENTS

| EP | 0336298 A | 10/1989 | | |
|---|---|---|---|---|
| EP | 0375156 A | 6/1990 | | |
| EP | 0465096 A | 1/1992 | | |
| WO | WO9961002 A | 12/1999 | | |
| WO | WO0033821 A | 6/2000 | | |
| WO | 00/33821 | * | 6/2000 | .................. 424/468 |
| WO | WO0035425 A | 6/2000 | | |
| WO | WO 200044353 A1 | * | 8/2000 | ............. A61K/9/00 |

* cited by examiner

*Primary Examiner*—Raymond Henley, III
*Assistant Examiner*—Amy Lewis
(74) *Attorney, Agent, or Firm*—Robin L. Teskin; Duane Morris, LLP

(57) ABSTRACT

The present invention relates to formulations comprising a therapeutically effective amount of pravastatin, or a pharmaceutically acceptable salt thereof, and methods of their use. The present formulations and methods are designed to release little or no pravastatin in the stomach but release a therapeutic amount of pravastatin in the small intestine, thereby limiting systemic exposure of the body to pravastatin and maximizing hepatic-specific absorption of the drug. The formulations and methods of the present invention are particularly useful for treating and/or preventing conditions that are benefited by decreasing levels of lipids and/or cholesterol in the body.

57 Claims, 2 Drawing Sheets

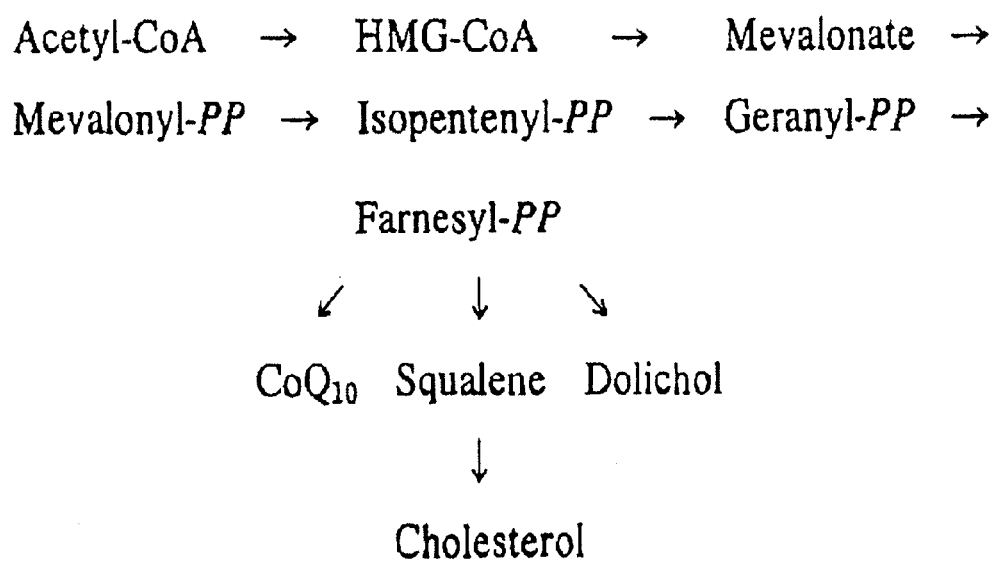
FIG. 1. Biosynthesis of cholesterol and coenzyme Q (CoQ) from acetyl-CoA. HMG-CoA, 3-hydroxy-3-methylglutaryl-coenzyme A; *PP*, pyrophosphate.

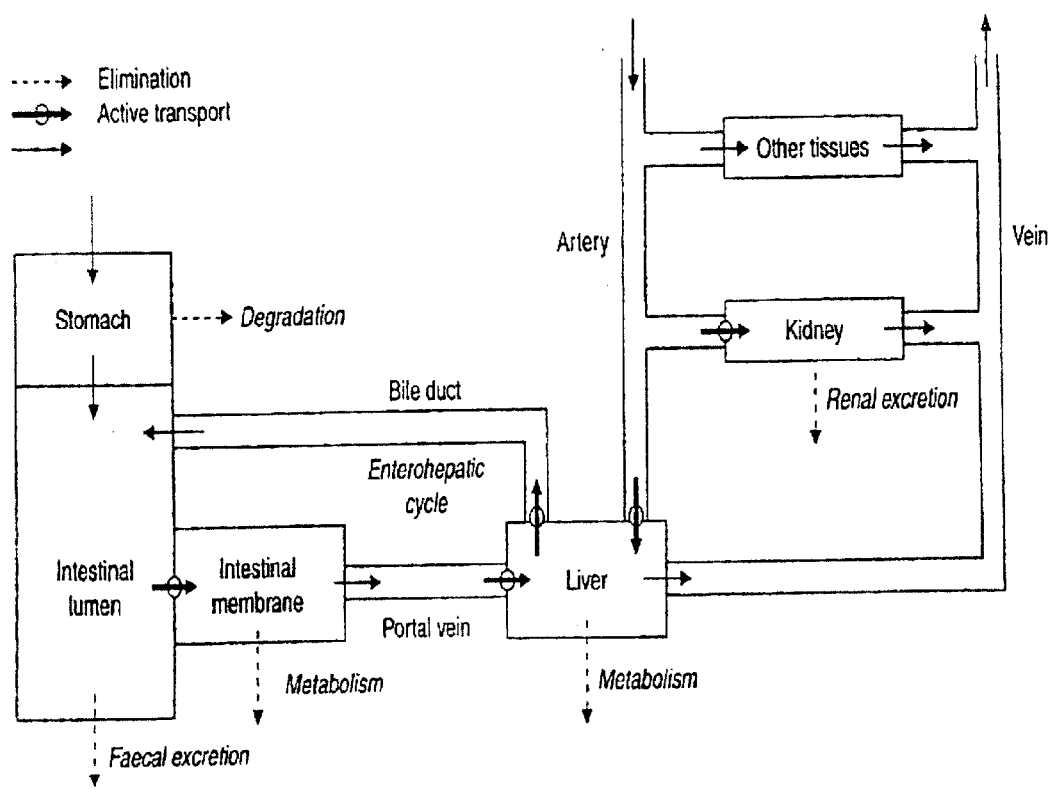
Figure 2 : Simplified view of the Pharmacokinetics of Pravastatin
(Reproduced from Hatanaka T, Clin. Pharmacokinet., 2000, 39 (6), 408)

PRAVASTATIN PHARMACEUTICAL FORMULATIONS AND METHODS OF THEIR USE

This application claims the benefit of priority of U.S. Provisional Patent Applications Nos. 60/347,775, filed Jan. 11, 2002, and 60/407,269, filed Sep. 3, 2002, the entire disclosure of each of which is incorporated by reference herein.

Pravastatin is an HMG-CoA reductase inhibitor that lowers blood lipid levels by reducing cholesterol biosynthesis in the liver. It is a competitive inhibitor of 3-hydroxy-3-methylglutaryl-co-enzyme A (HMG-CoA) reductase, which catalyzes the conversion of HMG-CoA to mevalonate, an early rate-limiting step in cholesterol biosynthesis.

Pravastatin sodium (sold as PRAVACHOL®) is commercially available for oral administration in 10 mg, 20 mg, 40 mg and 80 mg tablets. It is generally prescribed for lowering cholesterol and blood lipid levels. The drug has been found to be useful in preventing coronary events in hypercholesterolemic patients that do not have coronary heart disease and as a secondary preventative of coronary cardiovascular events in hypercholesterolemic patients that have coronary artery disease. The drug is also used as an adjunctive therapy (to supplement dietary restrictions and exercise) in reducing elevated Total-C, LDL-C, Apo B and TG levels, and to increase HDL-C levels in patients with primary hypercholesterolemia and mixed dyslipidemia (Fredrickson Type IIa and IIb), elevated serum triglyceride levels (Fredrickson Type IV), and primary dysbetalipoproteinemia (Fredrickson Type III) in patients who do not respond adequately to dietary restrictions.

Pravastatin sodium is typically administered orally in its active form. In clinical pharmacology studies in man, pravastatin is rapidly absorbed, with peak plasma levels of the drug attained 1 to 1.5 hours following ingestion. Based on urinary recovery of radiolabeled drug, the average oral absorption of pravastatin is 34% and absolute bioavailability is 17%. PRAVACHOL® Package Insert. While the presence of food in the gastrointestinal tract reduces systemic bioavailability, the lipid-lowering effects of the drug are similar whether taken with or 1 hour before meals. PRAVACHOL® Package Insert.

Pravastatin undergoes extensive first-pass extraction in the liver (extraction ratio 0.66), which is its primary site of action, and the primary site of cholesterol synthesis and LDL-C clearance. In vitro studies have shown that pravastatin is easily transported into hepatocytes with substantially less uptake into other cells. In view of pravastatin's extensive first-pass hepatic metabolism, plasma levels may not necessarily correlate with lipid-lowering efficacy. Pravastatin plasma concentrations (observed as: area under the concentration-time curve (AUC), peak ($C_{max}$), and steady-state minimum ($C_{min}$)) are directly proportional to administered dose. Systemic bioavailability of pravastatin administered following a bedtime (PM) dose was decreased 60% compared to the bioavailability following a morning (AM) dose.

Despite this decrease in systemic bioavailability, the efficacy of pravastatin administered in the evening was marginally more effective than the efficacy of the morning dose. This finding suggests that there is greater hepatic extraction of the drug when it is administered in the evening.

Pravastatin, like other HMG-CoA reductase inhibitors, has variable bioavailability. The coefficient of variation, based on between-subject variability, was 50% to 60% AUC. Approximately 20% of a radiolabeled oral dose is excreted in urine and 70% in the feces. After intravenous administration of radiolabeled pravastatin to normal healthy volunteers, approximately 47% of total body clearance was via renal excretion and 53% by non-renal routes, i.e., biliary excretion and biotransformation. Since there are dual routes of elimination, the potential exists both for compensatory excretion by the alternate route, as well as for accumulation of drug and/or metabolites in patients with renal or hepatic insufficiency.

Biotransformation pathways elucidated for pravastatin include: (a) isomerization to 6-epi pravastatin and the 3α-hydroxyisomer of pravastatin (SQ 31,906), (b) enzymatic ring hydroxylation to SQ 31,945, (c) ω-1 oxidation of the ester side chain, (d) β-oxidation of the carboxy side chain, (e) ring oxidation followed by aromatization, (f) oxidation of a hydroxyl group to a keto group, and (g) conjugation. The major degradation product is the 3α-hydroxy isomeric metabolite, which has one-tenth to one-fortieth the HMG-COA reductase inhibitory activity of the parent compound.

Pravastatin is absorbed from the intestine by a carrier-mediated mechanism. The absorption is not uniform throughout the intestinal tract; it is thought to largely occur in the small intestine, but the absorption is low in the distal small intestine (ileum) and colon (Lennernas & Fager, 1997). The uptake of pravastatin in the intestine takes place by an apparently saturable mechanism in the presence of a proton gradient; and the uptake is inhibited by monocarboxylic acids (Tamai et al, 1995).

Following absorption from the intestine, pravastatin is taken up into the liver by an active transport mechanism exhibiting a high hepatic extraction ratio (0.66) (Quion & Jones, 1994) or reasonably high hepatic extraction ratio (0.45) (Lennernas & Fager, 1997), which refers to the proportion of the drug that is extracted by the liver. This uptake of pravastatin into the hepatocytes may be mediated by a multispecific anion transporter (Yamazaki et al, 1993) believed to be OATP2 (Hsiang et al, 1999), and appears to be saturable (Nakai et al, 2001).

Pravastatin that is not absorbed by the hepatic system is delivered systemically to the rest of the body and can be detected in the blood plasma. Systemic pravastatin may cause unwanted effects in non-hepatic tissues. For example, one of the most significant adverse effects of HMG-CoA reductase inhibitors, such as pravastatin, is muscle necrosis, manifested as myalgia, limb weakness, elevation of serum creatinine kinase, and myoglobinuria (Rhabdomylosis) (Hunninghake, 1992). Severe myopathy has been observed in patients treated with pravastatin (Schalke et al, 1992).

Pravastatin is a relatively polar hydrophilic compound. FIG. 2 illustrates the fate of pravastatin in the body. The drug shows poor stability in acidic conditions, such as the environment of the stomach. If left unprotected, pravastatin undergoes non-enzymatic conversion in the stomach to a relatively inactive metabolite (Triscari et al, 1995).

Enteric coatings may be used to protect the drug from the acidic environment of the stomach. However, the coatings themselves often have acidic properties. As a result, pravastatin can be rendered less active by an acidic coating, reducing the overall efficacy of the treatment.

Enteric coatings can be combined with excipients having a basic pH. However, such basic excipients prevent optimal intestinal absorption, which occurs at a slightly acidic pH of about 5 in the intestine. To compensate for the inefficient absorption that occurs with basic excipients, higher concentrations of pravastatin must be provided in each dose.

Consequently, each dose is more expensive and a significant portion of the active ingredient never reaches the site of action in the liver.

Thus, there exists a need in the art for new pravastatin formulations that survive the acidic environment of the stomach, while allowing for more optimal absorption in the intestine and then in the liver.

Pravastatin inhibits HMG-CoA reductase, which is responsible for the conversion of HMG-CoA into mevalonate. Pravastatin interferes with cholesterol synthesis by inhibiting the formation of mevalonate, a cholesterol precursor. However, mevalonate is also a precursor of ubiquinone (Coenzyme Q), an essential component of the electron transport chain in mitochondria (Goldstein & Brown, 1990). FIG. 1 illustrates the biosynthesis of cholesterol and ubiquinone. Thus, pravastatin not only interferes with the biosynthesis of cholesterol, but also with other metabolic pathways that require mevalonate. Thus, in non-hepatic tissues, pravastatin may exert undesirable effects on important metabolic pathways. It is believed that pravastatin-mediated myopathy results from depletion of ubiquinone (coenzyme Q) levels in muscle tissue.

Again, there exists a need in the art for pravastatin formulations that limit systemic exposure of the body to pravastatin, and maximize hepatic-specific absorption of the drug, thus increasing the efficacy of pravastatin treatments and reducing undesirable side effects.

BRIEF DESCRIPTION OF THE DRAWINGS

FIG. 1 illustrates the biosynthesis of cholesterol and ubiquinone.

FIG. 2 illustrates the pharmacokinetics of pravastatin.

As used herein, the phrase "modified-release" formulation or dosage form includes a pharmaceutical preparation that achieves a desired release of the drug from the formulation. For example, a modified release formulation may extend the influence or effect of a therapeutically effective dose of an active compound in a patient. Such formulations are referred to herein as "extended-release" formulations. In addition to maintaining therapeutic levels of the active compound, a modified release formulation may also be designed to delay the release of the active compound for a specified period. Such compounds are referred to herein as "delayed onset" formulations or dosage forms. Still further, modified-release formulations may exhibit properties of both delayed and extended release formulations, and thus be referred to as "delayed-onset, extended-release" formulations.

As used herein, the term "conventional rapid release pravastatin formulation" means a formulation that, when tested in a USP dissolution bath in pH 6.8 buffer, releases greater than 80% of its content in less than about 1 hour.

As used herein, the term "pravastatin" includes pravastatin, and any pharmaceutically acceptable salts thereof.

As used herein, the term "pharmaceutically acceptable excipient" includes ingredients that are compatible with the other ingredients in a pharmaceutical formulation, in particular the active ingredients, and not injurious to the patient when administered in acceptable amounts.

As used herein, the term "pharmaceutically acceptable salt" includes salts that are physiologically tolerated by a patient. Such salts are typically prepared from inorganic acids or bases and/or organic acids or bases. Examples of these acids and bases are well known to those of ordinary skill in the art.

As used herein, "dicarboxylic acids" include, but are not limited to, 2-ethandioic (oxalic), 3-propandioic (malonic), 4-butandioic (succinic), 5-pentandioic (glutaric), 6-hexanedioic (adipic), cis-butenedioic (maleic), trans-butenedioic (fumaric), 2,3-dihydroxybutand ioic (tartaric), 2-hydroxy-1,2,3-propanetic carboxylic (citric), pimelic, suberic, azelaic, and sebacic acids.

As used herein, "monocarboxylic acids" include, but are not limited to, methanoic (formic), ethanoic (acetic), propanoic (propionic), butanoic (butyric), pentanoic (valeric), hexanoic (caproic), heptanoic (enanthic), 1-hydroxypropanoic (lactic), 3-benzyl-2-propenoic (cinnamic), and 2-oxopropanoic (pyruvic) acids.

As used herein, the phrase "therapeutically effective amount" includes the amount of pravastatin (or pharmaceutically acceptable salt thereof), which alone and/or in combination with other drugs, provides a benefit in the prevention, treatment, and/or management of one or more conditions or diseases that are associated with high cholesterol and/or high lipid levels or may otherwise benefit from a decrease in blood lipid levels or cholesterol levels. Such conditions or diseases include, but are not limited to, hypercholesterolemia, hyperlipidemia, myocardial infarction, stroke, ischemia, coronary atherosclerosis, coronary death, and/or cardiovascular mortality. In one embodiment, a therapeutically effective amount of pravastatin is the amount required to inhibit or reduce the activity of hepatic 3-hydroxy-3-methylglutaryl-co-enzyme A (HMG-CoA) reductase. The one or more diseases that can be treated, managed, and/or prevented by the formulations and/or methods of the present invention also include cardiovascular diseases that are not secondary to hypercholesterolemia.

The pravastatin methods and formulations of this invention may be administered with other drugs that are of therapeutic benefit in lowering lipid levels. Such drugs include other HMG CoA reductase inhibitors, such as atorvastatin, fluvastatin, simvastatin, or lovastatin, fibrates, such as gemfibrozil, modifiers of cholesterol absorption, such as ezetimibe, bile acid-binding resins, such as colestipol and cholestyramine, and/or other agents, such as fish oils, nicotinic acid, and probucol. The pravastatin formulations and methods of this invention, when co-administered with other lipid lowering agents, can be used to reduce the limiting side effects that may be observed when conventional rapid release pravastatin formulations are co-administered with other lipid lowering agents.

DESCRIPTION OF THE INVENTION

The present invention relates to compositions comprising a therapeutically effective amount of pravastatin, or a pharmaceutically acceptable salt thereof, and methods of their use. The compositions may be designed to minimize release of pravastatin in the stomach to avoid its conversion to inactive metabolites prior to absorption. Thus, when administered to a patient, the compositions of the present invention can delay the release of substantial amounts of pravastatin until the composition has passed out of the stomach and into the intestine.

The compositions of the present invention may also be designed to increase and/or optimize the hepatic-specific absorption of pravastatin from the intestine, thus limiting systemic exposure of the body to pravastatin and reducing at least one unwanted side effect that results from such exposure, e.g., when a conventional pravastatin formulation is administered. This is achieved by delivering pravastatin to the liver in a manner that is sufficient to provide a cholesterol-lowering effect for the subject receiving the drug, without inhibiting systemic synthesis of ubiquinone. In particular, the release of pravastatin from the compositions of the invention is targeted to the upper small intestine (the primary site of absorption), at a rate designed to avoid saturating the intestinal absorption apparatus.

The inventive compositions may also achieve a slower rate of absorption than conventional formulations, which improves delivery to the liver, such that the delivery rate is more consistent with the uptake rate into the hepatocytes. This can maximize uptake of pravastatin and maximize subsequent extraction by the liver, providing a dose-sparing effect. This can significantly reduce the amount of pravastatin diverted to the systemic circulation. While not wishing to be bound by any particular theory, compositions of the present invention may avoid the development of myopathy associated with undesirable depletion of ubiquinone in peripheral tissues.

Optimization of hepatic absorption also permits one to use less pravastatin in the compositions of the present invention, relative to the amounts required in conventional forms of the drug. Due to the more efficient delivery of pravastatin achieved by the present compositions, it is possible to decrease the amount of pravastatin included to about 10 to about 90%, about 10 to about 80%, about 10 to about 70%, about 20 to about 70%, about 20 to about 60%, or about 25 to about 50%, relative to a conventional formulation of the drug. In one embodiment, the amount of pravastatin in the composition of the present invention may be reduced to about 25%, relative to a dose of PRAVACHOL®.

The present invention also provides advantages in that equivalent, or higher, doses may be used, with better efficacy and/or fewer side effects observed. For example, pravastatin formulations of the present invention may include, for example, from 100% to 200% of the amount of pravastatin in conventional formulations. However, even with these higher doses, formulations of the present invention achieve better efficacy and fewer side effects.

The compositions of the present invention are suitable for treating and/or preventing conditions or diseases that are benefited by decreasing levels of lipids and/or cholesterol in the body. Such conditions include those that are typically treated and/or prevented with conventional pravastatin compositions, such as coronary events in hypercholesterolemic patients that lack clinically evident coronary heart disease, and coronary events in hypercholesterolemic patients that exhibit clinically evident coronary artery disease. The present compositions may also be used as an adjunctive therapy (to dietary restrictions and exercise) to reduce elevated total cholesterol (Total-C), low density lipoprotein-cholesterol (LDL-C), apolipoprotein B (Apo B), and triglyceride (TG) levels, and to increase high density lipoprotein-cholesterol (HDL-C) levels in subjects with primary hypercholesterolemia and mixed dyslipidemia (Fredrickson Type IIa and IIb), elevated serum triglyceride levels (Fredrickson Type IV), and primary dysbetalipoproteinemia (Fredrickson Type III), in patients that do not respond adequately to dietary restrictions. The present compositions and methods may also be used to treat, manage, and/or prevent one or more cardiovascular diseases that are not secondary to hypercholesterolemia.

The compositions of the present invention may be formulated into a dosage form that modifies the release of pravastatin. Examples of suitable modified release formulations, which may be used in accordance with the present invention include, but are not limited to, matrix systems, osmotic pumps, and membrane controlled dosage forms. These formulations of the present invention may comprise pravastatin or a pharmaceutically acceptable salt thereof. Suitable pharmaceutically acceptable salts are discussed above. Each of these types of dosage forms are briefly described below. A more detailed discussion of such forms may also be found in, for example *The Handbook of Pharmaceutical Controlled Release Technology*, D. L. Wise (ed.), Marcel Dekker, Inc., New York (2000); and also in *Treatise on Controlled Drug Delivery: Fundamentals, Optimization, and Applications*, A. Kydonieus (ed.), Marcel Dekker, Inc., New York, (1992), the relevant contents of each of which is hereby incorporated by reference for this purpose.

Matrix-Based Dosage Forms

In some embodiments, the modified release formulations of the present invention are provided as matrix-based dosage forms. Matrix formulations according to the invention may include hydrophilic, e.g., water-soluble, and/or hydrophobic, e.g., water-insoluble, polymers. The matrix formulations of the present invention may optionally be prepared with functional coatings, which may be enteric, e.g., exhibiting a pH-dependent solubility, or non-enteric, e.g., exhibiting a pH-independent solubility.

Matrix formulations of the present invention may be prepared by using, for example, direct compression or wet granulation. A functional coating, as noted above, may then be applied in accordance with the invention. Additionally, a barrier or sealant coat may be applied over a matrix tablet core prior to application of a functional coating. The barrier or sealant coat may serve the purpose of separating an active ingredient from a functional coating, which may interact with the active ingredient, or it may prevent moisture from contacting the active ingredient. Details of barriers and sealants are provided below.

In a matrix-based dosage form in accordance with the present invention, the pravastatin and optional pharmaceutically acceptable excipient(s) are dispersed within a polymeric matrix, which typically comprises one or more water-soluble polymers and/or one or more water-insoluble polymers. The drug may be released from the dosage form by diffusion and/or erosion. Such matrix systems are described in detail by Wise and Kydonieus, supra.

Suitable water-soluble polymers include, but are not limited to, polyvinyl alcohol, polyvinylpyrrolidone, methylcellulose, hydroxypropylcellulose, hydroxypropylmethyl cellulose or polyethylene glycol, and/or mixtures thereof.

Suitable water-insoluble polymers include, but are not limited to, ethylcellulose, cellulose acetate cellulose propionate, cellulose acetate propionate, cellulose acetate butyrate, cellulose acetate phthalate, cellulose triacetate, poly (methyl methacrylate), poly (ethyl methacrylate), poly (butyl methacrylate), poly (isobutyl methacrylate), and poly (hexyl methacrylate), poly (isodecyl methacrylate), poly (lauryl methacrylate), poly (phenyl methacrylate), poly (methyl acrylate), poly (isopropyl acrylate), poly (isobutyl acrylate), poly (octadecyl acrylate), poly (ethylene), poly (ethylene) low density, poly (ethylene) high density, poly (ethylene oxide), poly (ethylene terephthalate), poly (vinyl isobutyl ether), poly (vinyl acetate), poly (vinyl chloride) or polyurethane, and/or mixtures thereof.

Suitable pharmaceutically acceptable excipients include, but are not limited to, carriers, such as sodium citrate and dicalcium phosphate; fillers or extenders, such as stearates, silicas, gypsum, starches, lactose, sucrose, glucose, mannitol, talc, and silicic acid; binders, such as hydroxypropyl methylcellulose, hydroxymethyl-cellulose, alginates, gelatin, polyvinyl pyrrolidone, sucrose and acacia; humectants, such as glycerol; disintegrating agents, such as agar, calcium carbonate, potato and tapioca starch, alginic acid, certain silicates, EXPLOTAB™, crospovidone, and sodium carbonate; solution retarding agents, such as paraffin; absorption accelerators, such as quaternary ammonium compounds; wetting agents, such as cetyl alcohol and glycerol monostearate; absorbents, such as kaolin and bentonite clay; lubricants, such as talc, calcium stearate, magnesium stearate, solid polyethylene glycols, and sodium lauryl sulfate; stabilizers, such as fumaric acid; coloring agents; buffering agents; dispersing agents; preservatives; organic acids; and organic bases. The aforementioned excipients are given as examples only and are not meant to include all possible choices. Additionally, many excipients may have more than one role or function, or be classified in more than one group; the classifications are descriptive only, and not intended to limit any use of a particular excipient.

In one embodiment, a matrix-based dosage form comprises pravastatin; a filler, such as starch, lactose, or microcrystalline cellulose (AVICEL™); a binder/controlled-release polymer, such as hydroxypropyl methylcellulose or polyvinyl pyrrolidone; a disintegrant, such as, EXPLOTAB™, crospovidone, or starch; a lubricant, such as magnesium stearate or stearic acid; a surfactant, such as sodium lauryl sulfate or polysorbates; and a glidant, such as colloidal silicon dioxide (AEROSIL™) or talc.

The amounts and types of polymers, and the ratio of water-soluble polymers to water-insoluble polymers in the inventive formulations are generally selected to achieve a desired release profile of pravastatin, as described below. For example, by increasing the amount of water insoluble-polymer relative to the amount of water soluble-polymer, the release of the drug may be delayed or slowed. This is due, in part, to an increased impermeability of the polymeric matrix, and, in some cases, to a decreased rate of erosion during transit through the GI tract.

Osmotic Pump Dosage Forms

In another embodiment, the modified release formulations of the present invention are provided as osmotic pump dosage forms. In an osmotic pump dosage form, a core containing the pravastatin and optionally one or more osmotic excipients is typically encased by a selectively permeable membrane having at least one orifice. The selectively permeable membrane is generally permeable to water, but impermeable to the drug. When the system is exposed to body fluids, water penetrates through the selectively permeable membrane into the core containing the drug and optional osmotic excipients. The osmotic pressure increases within the dosage form. Consequently, the drug is released through the orifice(s) in an attempt to equalize the osmotic pressure across the selectively permeable membrane.

In more complex pumps, the dosage form may contain two internal compartments in the core. The first compartment contains the drug and the second compartment may contain a polymer, which swells on contact with aqueous fluid. After ingestion, this polymer swells into the drug-containing compartment, diminishing the volume occupied by the drug, thereby delivering the drug from the device at a controlled rate over an extended period of time. Such dosage forms are often used when a zero order release profile is desired.

Osmotic pumps are well known in the art. For example, U.S. Pat. Nos. 4,088,864, 4,200,098, and 5,573,776, each of which is hereby incorporated by reference for this purpose, describe osmotic pumps and methods of their manufacture. The osmotic pumps useful in accordance with the present invention may be formed by compressing a tablet of an osmotically active drug, or an osmotically inactive drug in combination with an osmotically active agent, and then coating the tablet with a selectively permeable membrane which is permeable to an exterior aqueous-based fluid but impermeable to the drug and/or osmotic agent.

One or more delivery orifices may be drilled through the selectively permeable membrane wall. Alternatively, one or more orifices in the wall may be formed by incorporating leachable pore-forming materials in the wall. In operation, the exterior aqueous-based fluid is imbibed through the selectively permeable membrane wall and contacts the drug to form a solution or suspension of the drug. The drug solution or suspension is then pumped out through the orifice as fresh fluid is imbibed through the selectively permeable membrane.

Typical materials for the selectively permeable membrane include selectively permeable polymers known in the art to be useful in osmosis and reverse osmosis membranes, such as cellulose acylate, cellulose diacylate, cellulose triacylate, cellulose acetate, cellulose diacetate, cellulose triacetate, agar acetate, amylose triacetate, beta glucan acetate, acetaldehyde dimethyl acetate, cellulose acetate ethyl carbamate, polyamides, polyurethanes, sulfonated polystyrenes, cellulose acetate phthalate, cellulose acetate methyl carbamate, cellulose acetate succinate, cellulose acetate dimethyl aminoacetate, cellulose acetate ethyl carbamate, cellulose acetate chloracetate, cellulose dipalmitate, cellulose dioctanoate, cellulose dicaprylate, cellulose dipentanlate, cellulose acetate valerate, cellulose acetate succinate, cellulose propionate succinate, methyl cellulose, cellulose acetate p-toluene sulfonate, cellulose acetate butyrate, lightly cross-linked polystyrene derivatives, cross-linked poly(sodium styrene sulfonate), poly(vinylbenzyltrimethyl ammonium chloride), cellulose acetate, cellulose diacetate, cellulose triacetate, and/or mixtures thereof.

The osmotic agents that can be used in the pump are typically soluble in the fluid that enters the device following administration, resulting in an osmotic pressure gradient across the selectively permeable wall against the exterior fluid. Suitable osmotic agents include, but are not limited to, magnesium sulfate, calcium sulfate, magnesium chloride, sodium chloride, lithium chloride, potassium sulfate, sodium carbonate, sodium sulfite, lithium sulfate, potassium chloride, sodium sulfate, d-mannitol, urea, sorbitol, inositol, raffinose, sucrose, glucose, hydrophilic polymers such as cellulose polymers, and/or mixtures thereof.

As discussed above, the osmotic pump dosage form may contain a second compartment containing a swellable polymer. Suitable swellable polymers typically interact with water and/or aqueous biological fluids, which causes them to swell or expand to an equilibrium state. Acceptable polymers exhibit the ability to swell in water and/or aqueous biological fluids, retaining a significant portion of such imbibed fluids within their polymeric structure, so as into increase the hydrostatic pressure within the dosage form. The polymers may swell or expand to a very high degree, usually exhibiting a 2- to 50-fold volume increase. The polymers can be non-cross-linked or cross-linked. In one embodiment, the swellable polymers are hydrophilic polymers. Suitable polymers include, but are not limited to, poly(hydroxy alkyl methacrylate) having a molecular weight of from 30,000 to 5,000,000; kappa-carrageenan; polyvinylpyrrolidone having a molecular weight of from 10,000 to 360,000; anionic and cationic hydrogels; polyelectrolyte complexes; poly(vinyl alcohol) having low amounts of acetate, cross-linked with glyoxal, formaldehyde, or glutaraldehyde, and having a degree of polymerization from 200 to 30,000; a mixture including methyl cellulose, cross-linked agar and carboxymethyl cellulose; a water-insoluble, water-swellable copolymer produced by forming a dispersion of finely divided maleic anhydride with styrene, ethylene, propylene, butylene or isobutylene; water-swellable polymers of N-vinyl lactams; and/or mixtures of any of the foregoing.

The term "orifice" as used herein comprises means and methods suitable for releasing the drug from the dosage form. The expression includes one or more apertures or orifices that have been bored through the selectively permeable membrane by mechanical procedures. Alternatively, an orifice may be formed by incorporating an erodible element, such as a gelatin plug, in the selectively permeable membrane. In such cases, the pores of the selectively permeable membrane form a "passageway" for the passage of the drug. Such "passageway" formulations are described, for example, in U.S. Pat. Nos. 3,845,770 and 3,916,899, the relevant disclosures of which are incorporated herein by reference for this purpose.

The osmotic pumps useful in accordance with this invention may be manufactured by techniques known in the art. For example, the drug and other ingredients may be milled together and pressed into a solid having the desired dimensions (e.g., corresponding to the first compartment). The swellable polymer is then formed, placed in contact with the drug, and both are surrounded with the selectively permeable agent. If desired, the drug component and polymer component may be pressed together before applying the selectively permeable membrane. The selectively permeable membrane may be applied by any suitable method, for example, by molding, spraying, or dipping.

Membrane-Controlled Dosage Forms

The modified release formulations of the present invention may also be provided as membrane controlled formulations. Membrane controlled formulations of the present invention can be made by preparing a rapid release core, which may be a monolithic (e.g., tablet) or multi-unit (e.g., pellet) type, and coating the core with a membrane. The membrane-controlled core can then be further coated with a functional coating. In between the membrane-controlled core and functional coating, a barrier or sealant may be applied. The barrier or sealant may alternatively, or additionally, be provided between the rapid release core and the membrane coating. Details of membrane-controlled dosage forms are provided below.

In one embodiment, the pravastatin is provided in a multiparticulate membrane controlled formulation. Pravastatin may be formed into an active core by applying the drug to a nonpareil seed having an average diameter in the range of about 0.4 to about 1.1 mm or about 0.85 to about 1.00 mm. The pravastatin may be applied with or without additional excipients onto the inert cores, and may be sprayed from solution or suspension using a fluidized bed coater (e.g., Wurster coating) or pan coating system. Alternatively, the pravastatin may be applied as a powder onto the inert cores using a binder to bind the pravastatin onto the cores. Active cores may also be formed by extrusion of the core with suitable plasticizers (described below) and any other processing aids as necessary.

The modified release formulations of the present invention comprise at least one polymeric material, which is applied as a membrane coating to the drug-containing cores. Suitable water-soluble polymers include, but are not limited to, polyvinyl alcohol, polyvinylpyrrolidone, methylcellulose, hydroxypropylcellulose, hydroxypropylmethyl cellulose or polyethylene glycol, and/or mixtures thereof.

Suitable water-insoluble polymers include, but are not limited to, ethylcellulose, cellulose acetate cellulose propionate, cellulose acetate propionate, cellulose acetate butyrate, cellulose acetate phthalate, cellulose triacetate, poly (methyl methacrylate), poly (ethyl methacrylate), poly (butyl methacrylate), poly (isobutyl methacrylate), and poly (hexyl methacrylate), poly (isodecyl methacrylate), poly (lauryl methacrylate), poly (phenyl methacrylate), poly (methyl acrylate), poly (isopropyl acrylate), poly (isobutyl acrylate), poly (octadecyl acrylate), poly (ethylene), poly (ethylene) low density, poly (ethylene) high density, poly (ethylene oxide), poly (ethylene terephthalate), poly (vinyl isobutyl ether), poly (vinyl acetate), poly (vinyl chloride) or polyurethane, and/or mixtures thereof.

EUDRAGIT™ polymers (available from Rohm Pharma) are polymeric lacquer substances based on acrylates and/or methacrylates. A suitable polymer that is freely permeable to the active ingredient and water is EUDRAGIT™ RL. A suitable polymer that is slightly permeable to the active ingredient and water is EUDRAGIT™ RS. Other suitable polymers which are slightly permeable to the active ingredient and water, and exhibit a pH-dependent permeability include, but are not limited to, EUDRAGIT™ L, EUDRAGIT™ S, and EUDRAGIT™ E.

EUDRAGIT™ RL and RS are acrylic resins comprising copolymers of acrylic and methacrylic acid esters with a low content of quaternary ammonium groups. The ammonium groups are present as salts and give rise to the permeability of the lacquer films. EUDRAGIT™ RL and RS are freely permeable (RL) and slightly permeable (RS), respectively, independent of pH. The polymers swell in water and digestive juices, in a pH-independent manner. In the swollen state, they are permeable to water and to dissolved active compounds.

EUDRAGIT™ L is an anionic polymer synthesized from methacrylic acid and methacrylic acid methyl ester. It is insoluble in acids and pure water. It becomes soluble in neutral to weakly alkaline conditions. The permeability of EUDRAGIT™ L is pH dependent. Above pH 5.0, the polymer becomes increasingly permeable.

In one embodiment comprising a membrane-controlled dosage form, the polymeric material comprises methacrylic acid co-polymers, ammonio methacrylate co-polymers, or a mixture thereof. Methacrylic acid co-polymers such as EUDRAGIT™ S and EUDRAGIT™ L (Rohm Pharma) are particularly suitable for use in the controlled release formulations of the present invention. These polymers are gastroresistant and enterosoluble polymers. Their polymer films are insoluble in pure water and diluted acids. They dissolve at higher pHs, depending on their content of carboxylic acid. EUDRAGIT™ S and EUDRAGIT™ L can be used as single components in the polymer coating or in combination in any ratio. By using a combination of the polymers, the polymeric material may exhibit a solubility at a pH between the pHs at which EUDRAGIT™ L and EUDRAGIT™ S are separately soluble.

The membrane coating may comprise a polymeric material comprising a major proportion (i.e., greater than 50% of the total polymeric content) of one or more pharmaceutically acceptable water-soluble polymers, and optionally a minor proportion (i.e., less than 50% of the total polymeric content) of one or more pharmaceutically acceptable water insoluble polymers. Alternatively, the membrane coating may comprise a polymeric material comprising a major proportion (i.e., greater than 50% of the total polymeric content) of one or more pharmaceutically acceptable water insoluble polymers, and optionally a minor proportion (i.e., less than 50% of the total polymeric content) of one or more pharmaceutically acceptable water-soluble polymers.

Ammonio methacrylate co-polymers such as Eudragit RS and Eudragit RL (Rohm Pharma) are suitable for use in the controlled release formulations of the present invention. These polymers are insoluble in pure water, dilute acids, buffer solutions, or digestive fluids over the entire physiological pH range. The polymers swell in water and digestive fluids independently of pH. In the swollen state they are then permeable to water and dissolved actives. The permeability of the polymers depends on the ratio of ethylacrylate (EA), methyl methacrylate (MMA), and trimethylammonioethyl methacrylate chloride (TAMCl) groups in the polymer. Those polymers having EA:MMA:TAMCl ratios of 1:2:0.2 (Eudragit RL) are more permeable than those with ratios of 1:2:0.1 (Eudragit RS). Polymers of Eudragit RL are insoluble polymers of high permeability. Polymers of Eudragit RS are insoluble films of low permeability.

The ammonio methacrylate co-polymers may be combined in any desired ratio. For example, a ratio of Eudragit RS:Eudragit RL (90:10) may be used. The ratios may furthermore be adjusted to provide a delay in release of the drug. For example, the ratio of Eudragit RS:Eudragit RL may be about 100:0 to about 80:20, about 100:0 to about 90:10, or any ratio in between. In such formulations, the less permeable polymer Eudragit RS would generally comprise the majority of the polymeric material.

The ammonio methacrylate co-polymers may be combined with the methacrylic acid co-polymers within the polymeric material in order to achieve the desired delay in release of the drug. Ratios of ammonio methacrylate co-polymer (e.g., Eudragit RS) to methacrylic acid co-polymer in the range of about 99:1 to about 20:80 may be used. The two types of polymers can also be combined into the same polymeric material, or provided as separate coats that are applied to the core.

In addition to the Eudragit polymers described above, a number of other such copolymers may be used to control drug release. These include methacrylate ester co-polymers (e.g., Eudragit NE 30D). Further information on the Eudragit polymers can be found in "Chemistry and Application Properties of Polymethacrylate Coating Systems," in *Aqueous Polymeric Coatings for Pharmaceutical Dosage Forms*, ed. James McGinity, Marcel Dekker Inc., New York, pg 109–114)

In addition to the Eudragit polymers discussed above, other enteric, or pH-dependent, polymers may be used. Such polymers may include phthalate, butyrate, succinate, and/or mellitate groups. Such polymers include, but are not limited to, cellulose acetate phthalate, cellulose acetate succinate, cellulose hydrogen phthalate, cellulose acetate trimellitate, hydroxypropyl-methylcellulose phthalate, hydroxypropylmethylcellulose acetate succinate, starch acetate phthalate, amylose acetate phthalate, polyvinyl acetate phthalate, and polyvinyl butyrate phthalate.

The coating membrane may further comprise one or more soluble excipients so as to increase the permeability of the polymeric material. Suitably, the soluble excipient is selected from among a soluble polymer, a surfactant, an alkali metal salt, an organic acid, a sugar, and a sugar alcohol. Such soluble excipients include, but are not limited to, polyvinyl pyrrolidone, polyethylene glycol, sodium chloride, surfactants such as sodium lauryl sulfate and polysorbates, organic acids such as acetic acid, adipic acid, citric acid, fumaric acid, glutaric acid, malic acid, succinic acid, and tartaric acid, sugars such as dextrose, fructose, glucose, lactose and sucrose, sugar alcohols such as lactitol, maltitol, mannitol, sorbitol and xylitol, xanthan gum, dextrins, and maltodextrins. In some embodiments, polyvinyl pyrrolidone, mannitol, and/or polyethylene glycol can be used as soluble excipients. The soluble excipient(s) may be used in an amount of from about 1% to about 10% by weight, based on the total dry weight of the polymer.

In another embodiment, the polymeric material comprises one or more water-insoluble polymers, which are also insoluble in gastrointestinal fluids, and one or more water-soluble pore-forming compounds. For example, the water-insoluble polymer may comprise a terpolymer of polyvinylchloride, polyvinylacetate, and/or polyvinylalcohol. Suitable water-soluble pore-forming compounds include, but are not limited to, saccharose, sodium chloride, potassium chloride, polyvinylpyrrolidone, and/or polyethyleneglycol. The pore-forming compounds may be uniformly or randomly distributed throughout the water insoluble polymer. Typically, the pore-forming compounds comprise about 1 part to about 35 parts for each about 1 to about 10 parts of the water insoluble polymers.

When such dosage forms come in to contact with the dissolution media (e.g., intestinal fluids), the pore-forming compounds within the polymeric material dissolve to produce a porous structure through which the drug diffuses. Such formulations are described in more detail in U.S. Pat. No. 4,557,925, which relevant part is incorporated herein by reference for this purpose. The porous membrane may also be coated with an enteric coating, as described herein, to inhibit release in the stomach.

In one embodiment, such pore forming controlled release dosage forms comprise pravastatin; a filler, such as starch, lactose, or microcrystalline cellulose (AVICEL™); a binder/controlled release polymer, such as hydroxypropyl methylcellulose or polyvinyl pyrrolidone; a disintegrant, such as, EXPLOTAB™, crospovidone, or starch; a lubricant, such as magnesium stearate or stearic acid; a surfactant, such as sodium lauryl sulphate or polysorbates; and a glidant, such as colloidal silicon dioxide (AEROSIL™) or talc.

The polymeric material may also include one or more auxiliary agents such as fillers, plasticizers, and/or anti-foaming agents. Representative fillers include talc, fumed silica, glyceryl monostearate, magnesium stearate, calcium stearate, kaolin, colloidal silica, gypsum, micronized silica, and magnesium trisilicate. The quantity of filler used typically ranges from about 2% to about 300% by weight, and can range from about 20 to about 100%, based on the total dry weight of the polymer. In one embodiment, talc is the filler.

The coating membranes, and functional coatings as well, can also include a material that improves the processing of the polymers. Such materials are generally referred to as plasticizers and include, for example, adipates, azelates, benzoates, citrates, isoebucates, phthalates, sebacates, stearates and glycols. Representative plasticizers include acetylated monoglycerides, butyl phthalyl butyl glycolate, dibutyl tartrate, diethyl phthalate, dimethyl phthalate, ethyl phthalyl ethyl glycolate, glycerin, ethylene glycol, propylene glycol, triacetin citrate, triacetin, tripropinoin, diacetin, dibutyl phthalate, acetyl monoglyceride, polyethylene glycols, castor oil, triethyl citrate, polyhydric alcohols, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidised tallate, triisoctyl trimellitate, diethylhexyl phthalate, di-n-octyl phthalate, di-i-octyl phthalate, di-i-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate, glyceryl monocaprylate, and glyceryl monocaprate. In one embodiment, the plasticizer is dibutyl sebacate. The amount of plasticizer used in the polymeric material typically ranges from about 10% to about 50%, for example, about 10, 20, 30, 40, or 50%, based on the weight of the dry polymer.

Anti-foaming agents can also be included. In one embodiment, the anti-foaming agent is simethicone. The amount of anti-foaming agent used typically comprises from about 0% to about 0.5% of the final formulation.

The amount of polymer to be used in the membrane controlled formulations is typically adjusted to achieve the desired drug delivery properties, including the amount of drug to be delivered, the rate and location of drug delivery, the time delay of drug release, and the size of the multiparticulates in the formulation. The amount of polymer applied typically provides an about 10 to about 100% weight gain to the cores. In one embodiment, the weight gain from the polymeric material ranges from about 25 to about 70%.

A polymeric membrane may include components in addition to polymers, such as, for example, fillers, plasticizers, stabilizers, or other excipients and processing aids. One example of an additional component of the membrane is sodium hydrogen carbonate, which may act as a stabilizer.

The combination of all solid components of the polymeric material, including co-polymers, fillers, plasticizers, and optional excipients and processing aids, typically provides an about 10 to about 450% weight gain on the cores. In one embodiment, the weight gain is about 30 to about 160%.

The polymeric material can be applied by any known method, for example, by spraying using a fluidized bed coater (e.g., Wurster coating) or pan coating system. Coated cores are typically dried or cured after application of the polymeric material. Curing means that the multiparticulates are held at a controlled temperature for a time sufficient to provide stable release rates. Curing can be performed, for example, in an oven or in a fluid bed drier. Curing can be carried out at any temperature above room temperature.

A sealant or barrier can also be applied to the polymeric coating. Alternatively, or additionally, a sealant or barrier layer may be applied to the core prior to applying the polymeric material. A sealant or barrier layer is generally not intended to modify the release of pravastatin. Suitable sealants or barriers are permeable or soluble agents such as hydroxypropyl methylcellulose, hydroxypropyl cellulose, hydroxypropyl ethylcellulose, polyvinyl pyrrolidone, and xanthan gum. An outer sealant/barrier, for example, might be used to improve moisture resistance of the entire formulation. A sealant/barrier between the core and the coating, for example, might be used to protect the core contents from an outer polymeric coating that may exhibit pH-dependent or pH-independent dissolution properties. Additionally, there may be instances in which both effects are desired, i.e., moisture resistance and core protection, in which a sealant/barrier is applied between the core and the polymeric membrane coating, and then outside the polymeric membrane coating.

Other agents can be added to improve the processability of a sealant or barrier layer. Such agents include talc, colloidal silica, polyvinyl alcohol, titanium dioxide, micronized silica, fumed silica, glycerol monostearate, magnesium trisilicate and magnesium stearate, or a mixture thereof. The sealant or barrier layer can be applied from solution (e.g., aqueous) or suspension using any known means, such as a fluidized bed coater (e.g., Wurster coating) or pan coating system. Suitable sealants or barriers include, for example, OPADRY WHITE Y-1-7000 and OPADRY OY/B/28920 WHITE, each of which is available from Colorcon Limited, England.

The invention also provides an oral dosage form containing a multiparticulate pravastatin formulation as hereinabove defined, in the form of caplets, capsules, particles for suspension prior to dosing, sachets, or tablets. When the dosage form is in the form of tablets, the tablets may be disintegrating tablets, fast dissolving tablets, effervescent tablets, fast melt tablets, and/or mini-tablets. The dosage form can be of any shape suitable for oral administration of a drug, such as spheroidal, cube-shaped oval, or ellipsoidal. The dosage forms can be prepared from the multiparticulates in a manner known in the art and include additional pharmaceutically acceptable excipients, as desired.

Soft Gelatin Capsules

The formulations of the present invention may also be prepared as liquids, which may be filled into soft gelatin capsules. For example, the liquid may include a solution, suspension, emulsion, microemulsion, precipitate, or any other desired liquid media carrying the statin(s). The liquid may be designed to improve the solubility of the statin(s) upon release, or may be designed to form a drug-containing emulsion or dispersed phase upon release. Examples of such techniques are well known in the art. Soft gelatin capsules may be coated, as desired, with a functional coating to delay the release of the drug.

All of the particular embodiments described above, including but not limited to, matrix-based, osmotic pump-based, soft gelatin capsules, and/or membrane-controlled forms, which may further take the form of monolithic and/or multi-unit dosage forms, may have a functional coating. Such coatings generally serve the purpose of delaying the release of the drug for a predetermined period. For example, such coatings may allow the dosage form to pass through the stomach without being subjected to stomach acid or digestive juices. Thus, such coatings may dissolve or erode upon reaching a desired point in the gastrointestinal tract, such as the upper intestine.

Such functional coatings may exhibit pH-dependent or pH-independent solubility profiles. Those with pH-independent profiles generally erode or dissolve away after a predetermined period, and the period is generally related to the thickness and composition of the coating. Those with pH-dependent profiles, on the other hand, may maintain their integrity while in the acid pH of the stomach, but quickly erode or dissolve upon entering the more basic upper intestine.

Thus, a matrix-based, osmotic pump-based, or membrane-controlled formulation may be further coated with a functional coating that delays the release of the drug. For example, a membrane-controlled formulation may be coated with an enteric coating that delays the exposure of the membrane-controlled formulation until the upper intestine is reached. Upon leaving the acidic stomach and entering the more basic intestine, the enteric coating dissolves. The membrane-controlled formulation then is exposed to gastrointestinal fluid, and then releases the pravastatin over an extended period, in accordance with the invention. Examples of functional coatings such as these are well known to those in the art.

In one embodiment, the pravastatin formulations initially delay the release of the drug. Following the delay, the formulation may rapidly release the drug. Such formulations would provide a more rapid and/or immediate therapeutic effect for the subject.

Formulations of the present invention may further comprise pH-modifying agents, for example, agents exhibiting a pKa of from about 1 to about 6.5. Such agents include, but are not limited to, dicarboxylic acids. Dicarboxylic acids include, but are not limited to, 2-ethandioic (oxalic), 3-propandioic (malonic), 4-butandioic (succinic), 5-pentandioic (glutaric), 6-hexandioic (adipic), cis-butenedioic (maleic), trans-butenedioic (fumaric), 2,3-dihydroxybutandioic (tartaric), 2-hydroxy-1,2,3-propanetic carboxylic (citric), pimelic, suberic, azelaic, and sebacic acids. In some embodiments, one or more dicarboxylic acids is included in the formulation.

In some embodiments, the formulation is substantially free from monocarboxylic acids. As used in this context, "substantially free" means that monocarboxylic acids are not added to the formulation, but may be present otherwise. Monocarboxylic acids include, but are not limited to, methanoic (formic), ethanoic (acetic), propanoic (propionic), butanoic (butyric), pentanoic (valeric), hexanoic (caproic), heptanoic (enanthic), 1-hydroxypropanoic (lactic), 3-benzyl-2-propenoic (cinnamic), and 2-oxopropanoic (pyruvic) acids.

The formulations of the present invention may include pH-modifying agents that create a microenvironment around the pravastatin when exposed to aqueous fluids. For example, these agents may create a microenvironment around the pravastatin having a pH of from about 3 to about 6, or, for example, a pH of about 5.

Simply put, the formulations and methods of the present invention deliver a therapeutic dose into the environment of use, which is the small intestine. The methods and formulations of the invention are designed to avoid release in the stomach, but then exhibit a controlled but complete release in the small intestine. As it is believed that pravastatin absorption occurs almost entirely in the small intestine, and that absorption from the large intestine is negligible, the methods and formulations of this invention are designed to release solely in the small intestine. Thus, absorption efficiency is maximized, and little drug is wasted.

The methods and formulations of the present invention generally exhibit the following characteristics upon administration to the patient:
(i) minimal or no release for up to about 2 hours, followed by
(ii) an extended release over about 2 to about 6 hours.

Described another way, the formulations and methods of the present invention generally exhibit the following characteristics upon administration to the patient:
(i) minimal or no release in the stomach, followed by
(ii) controlled but complete release into the small intestine.

Thus, some methods and formulations of the present invention completely release pravastatin into the environment of use in less than about six hours. That is, greater than 80% is released by a time prior to about 6 hours following administration. "Completely released" means greater than 80% of the pravastatin in the formulation is released.

Absolute systemic bioavailability from PRAVACHOL® is about 17%. Using the compositions of the present invention, systemic bioavailability of pravastatin may be reduced to below about 17%, for example, about 15%, 10%, 5%, or 0%, or any amount less than about 17%. As compared to PRAVACHOL®, or any conventional rapid release pravastatin formulation, administration of the compositions of the present invention achieves a decrease in the systemic bioavailability to less than about 90%, 80%, 70%, 60%, 50%, 40%, 30%, or 25%, of that of the conventional formulation. This is referred to herein as the "relative" systemic bioavailability.

Hepatic extraction of pravastatin from PRAVACHOL® ranges from about 45 to about 65%. Using the compositions of the present invention, hepatic extraction of pravastatin may be increased to greater than about 45–65%, for example, to about 50%, 55%, 60%, 65%, 70%, 75%, 80%, 85%, 90%, 95%, or 100%, or any amount above about 45%.

Variability in AUC from PRAVACHOL® is about 50 to about 60%. Using the compositions of the present invention, variability in AUC may be reduced to below about 50–60%, for example, about 40% to about 50%, about 30% to about 40%, or about 20% to about 30%, or any variability less than about 60%.

The peak plasma concentration, or Cmax, may be reduced by the formulations and compositions of the present invention, as compared to PRAVACHOL®, or any conventional rapid release pravastatin formulation. For example, as compared to the Cmax resulting from the use of PRAVACHOL®, or any conventional rapid release pravastatin formulation, the Cmax may be reduced to less than about 80%, 70%, 60%, 50%, 40%, 30%, or 25%. This is referred to herein as the "relative" Cmax.

The therapeutic level is the minimum concentration of pravastatin that is therapeutically effective in a particular patient. Of course, one of skill in the art will recognize that the therapeutic level may vary depending on the individual being treated and the severity of the condition. For example, the age, body weight, and medical history of the individual patient may affect the therapeutic efficacy of the therapy. A competent physician can consider these factors and adjust the dosing regimen to ensure the dose is achieving the desired therapeutic outcome without undue experimentation. It is also noted that the clinician and/or treating physician will know how and when to interrupt, adjust, and/or terminate therapy in conjunction with individual patient response.

In general, the total daily dosage of pravastatin in formulations of the present invention ranges from about 1 mg to about 200 mg, about 1 to about 160 mg, about 1 to about 80 mg, about 5 to about 80 mg, about 10 to about 80 mg, or any whole number or fractional amount in between. A single dose may be formulated to contain about 1, 5, 10, 15, 20, 25, 30, 35, 40, 60, 80, 100, 120, 140, 160, 180, or 200 mg of pravastatin. In one embodiment, a single dose contains about 5, 10, 15, 20, 40, 60, or 80 mg of pravastatin.

The formulations of the present invention may be described by their dissolution profiles. One of skill in the art is familiar with the techniques used to determine such dissolution profiles. The standard methodologies set forth in the U.S. Pharmacopoeia, which methodologies are incorporated herein by reference in relevant part, may be used. For example, the dissolution profile may be measured in either a U.S. Pharmacopoeia Type I Apparatus (baskets) or a U.S. Pharmacopoeia Type II Apparatus (paddles). For pH-independent formulations, the formulations may be tested in phosphate buffer at pH 6.8 or higher, 37° C., and 50–100 rpm. For pH-dependent formulations, the formulations may be tested in 0.01–0.1 N HCl for the first 2 hours at 37° C. and 50–100 rpm, followed by transfer to phosphate buffer at pH 6.8 or higher for the remainder of the test. Other buffer systems suitable for measuring the dissolution profile for pH-dependent and pH-independent formulations are well known to those of skill in the art.

The in vitro dissolution profile of pH-dependent pravastatin compositions of the present invention may correspond to the following, when tested in acid for 2 hours followed by pH 6.8 or higher buffer:
(1) minimal release after about 2 hours; and
(2) complete release after about 8 hours.
Alternatively, the profile may correspond to:
(1) less than about 20% of the pravastatin is released after about 2 hours;

(2) about 20% to about 80% is released after about 4 hours; and
(3) greater than about 60% is released after about 6–8 hours.

The in vitro dissolution profile of pH-dependent formulations of the invention may correspond to the following, when tested for the entire period in buffer:
(1) complete release in about 6–8 hours.
Alternatively, the profile may correspond to:
(1) greater than or equal to about 50% released after about 4 hours; and
(2) greater than about 60% after about 6–8 hours.

The in vitro dissolution profile of pH-independent pravastatin compositions of the present invention may correspond to the following:
(1) minimal release after about 1–2 hours; and
(2) complete release after about 8 hours.
Alternatively, the profile may correspond to:
(1) less than about 20% of the pravastatin is released after about 1–2 hours;
(2) about 20% to about 80% is released after about 3–4 hours; and
(3) greater than about 60% is released after about 6–8 hours.

The dissolution profiles of the present modified release pravastatin formulations may substantially mimic one or more of the profiles provided below, based on in vitro release rates. For pH dependent formulations, release of the drug from the formulations may be retarded in acid for 1–2 hours. In pH 6.8 or higher buffer, the release of the drug is in a manner consistent with transit into the small intestine, the site of absorption of pravastatin. For pH independent formulations, release of the drug from the formulations is retarded for 1–2 hours, independent of the pH of the dissolution medium. After 1–2 hours, which coincides with emptying of the dosage form from the stomach into the small intestine, the drug is released in a manner consistent with transit of the dosage form through the small intestine, the site of absorption of pravastatin. The release profiles are obtained using either paddles at 50–75 rpm or baskets at 100 rpm.

| Time (hours) | % Released |
| --- | --- |
| acid | |
| 1.0–2.0 | ≦ about 20% |
| pH 6.8 | |
| 2.0 | ≧ about 20% |
| 4.0 | ≧ about 40% |
| 6.0 | ≧ about 60% |
| 12.0 | ≧ about 80% |

Alternatively, the following release profile may be achieved:

| Time (hours) | % Released |
| --- | --- |
| acid | |
| 1.0–2.0 | ≦ about 5% |
| pH 6.8 | |
| 1.0 | about 10–40% |
| 2.0 | about 30–70% |
| 3.0 | ≧ about 45% |
| 5.0 | ≧ about 80% |

In some embodiments, the pravastatin formulations may be prepared with a polymeric coating that exhibits a pH-dependent dissolution profile. Such formulations may exhibit a pravastatin release rate, as measured in a Type II dissolution apparatus, in a pH 6.8 buffer, of the following: 2 hours: greater than or equal to about 20%; 4 hours: greater than or equal to about 40%; 6 hours: greater than about 60%; and 12 hours: greater than or equal to about 80%. Such formulations may exhibit a pravastatin release rate, as measured in a Type II dissolution apparatus, in a pH 6.8 buffer, of the following: 1 hour: about 0 to about 50%; 2 hours: about 20 to about 80%; 4 hours: greater than or equal to about 50%; 6 hours: greater than or equal to about 70%; and 12 hours: greater than or equal to about 80%.

In other embodiments, the formulations may exhibit a pravastatin release rate, as measured in a Type II dissolution apparatus, in a pH 6.8 buffer, of the following: 1 hour: about 10 to about 40%; 2 hours: about 30 to about 70%; 3 hours: greater than or equal to about 45%; 4 hours: greater than or equal to about 60%; 5 hours: greater than or equal to about 75%; and 6 hours: greater than or equal to about 80%. Such formulations may exhibit a pravastatin release rate, as measured in a Type II dissolution apparatus, in a pH 6.8 buffer, of the following: 1 hour: about 10 to about 40%; 2 hours: about 30 to about 70%; 3 hours: greater than or equal to about 45%; 4 hours: greater than or equal to about 60%; and 5 hours: greater than or equal to about 80%.

When measured in a Type II dissolution apparatus, in a 0.01 to 0.1 N HCl medium for 2 hours, followed by pH 6.8 (or higher) buffer for the remainder of the test, formulations of the inventions with such pH-dependent coatings may exhibit the following dissolution profile: 2 hours (in HCl): less than or equal to about 20%; 2 hours (in pH 6.8 or higher): greater than or equal to about 20%; 4 hours (in pH 6.8 or higher): greater than or equal to about 40%; 6 hours (in pH 6.8 or higher): greater than or equal to about 60%; and 12 hours (in pH 6.8 or higher): greater than or equal to about 80%. Such formulations may exhibit the following dissolution profile, when measured in a Type II dissolution apparatus, in a 0.01 to 0.1 N HCl medium for 2 hours, followed by pH 6.8 or higher buffer for the remainder of the test: 2 hours (in HCl): less than or equal to about 20%; 1 hour (in pH 6.8 or higher): about 0 to about 50%; 2 hours (in pH 6.8 or higher): about 20 to about 80%; 4 hours (in pH 6.8 or higher): greater than or equal to about 50%; 6 hours (in pH 6.8 or higher): greater than or equal to about 70%; and 12 hours (in pH 6.8 or higher): greater than or equal to about 80%.

In other embodiments, the formulation, when measured in a Type II dissolution apparatus, in a 0.01 to 0.1 N HCl medium for 2 hours, followed by pH 6.8 or higher buffer for the remainder of the test, formulations of the inventions with such pH-dependent coatings, may exhibit the following dissolution profile: 2 hours (in HCl): less than or equal to about 10%; 1 hour (in pH 6.8 or higher): about 10 to about 40%; 2 hours (in pH 6.8 or higher): about 30 to about 70%; 3 hours (in pH 6.8 or higher): greater than or equal to about 45%; 4 hours (in pH 6.8 or higher): greater than or equal to about 60%; 5 hours (in pH 6.8 or higher): greater than or equal to about 75%; and 6 hours (in pH 6.8 or higher): greater than or equal to about 80%. Such formulations may exhibit the following dissolution profile, when measured in a Type II dissolution apparatus, in a 0.01 to 0.1 N HCl medium for 2 hours, followed by pH 6.8 or higher buffer for the remainder of the test: 2 hours (in HCl): less than or equal to about 5%; 1 hour (in pH 6.8 or higher): about 10 to about 40%; 2 hours (in pH 6.8 or higher): about 30 to about 70%; 3 hours (in pH 6.8 or higher): greater than or equal to about 45%; 4 hours (in pH 6.8 or higher): greater than or equal to about 60%; and 5 hours (in pH 6.8 or higher): greater than or equal to about 80%.

In some embodiments, the pravastatin formulations may be prepared with a polymeric coating that exhibits a pH-independent dissolution profile. Such formulations may exhibit a pravastatin release rate, as measured in a Type II dissolution apparatus, in a pH 6.8 buffer, of the following: 1 hour: less than or equal to about 20%; 3 hours: greater than or equal to about 20%; 5 hours: greater than or equal to about 40%; 7 hours: greater than or equal to about 60%; and 12 hours: greater than or equal to about 80%. Such formulations may exhibit a pravastatin release rate, as measured in a Type II dissolution apparatus, in a pH 6.8 buffer, of the following: 1 hour: less than or equal to about 20%; 2 hours: about 0 to about 50%; 3 hours: about 20 to about 80%; 5 hours: greater than or equal to about 50%; 7 hours: greater than or equal to about 70%; and 12 hours: greater than or equal to about 80%.

In other embodiments, the pH-independent formulations may exhibit a pravastatin release rate, as measured in a Type II dissolution apparatus, in a pH 6.8 buffer, of the following: 1 hour: less than or equal to about 10%; 2 hours: about 10 to about 40%; 3 hours: about 30 to about 70%; 4 hours: greater than or equal to about 45%; 5 hours: greater than or equal to about 60%; 6 hours: greater than or equal to about 75%; and 7 hours: greater than or equal to about 80%. Such formulations may exhibit a pravastatin release rate, as measured in a Type II dissolution apparatus, in a pH 6.8 buffer, of the following: 1 hour: less than or equal to about 5%; 2 hours: about 10 to about 40%; 3 hours: about 30 to about 70%; 4 hours: greater than or equal to about 45%; 5 hours: greater than or equal to about 60%; and 6 hours: greater than or equal to about 80%.

Any of the pharmaceutical compositions described above may further comprise one or more pharmaceutically active compounds other than pravastatin. Such compounds may be provided to treat the same condition being treated with pravastatin, or a different one. Those of skill in the art are familiar with examples of techniques for incorporating additional active ingredients into the formulations of the present invention. Alternatively, such additional pharmaceutical compounds may be provided in a separate formulation and co-administered to a patient with a pravastatin composition. Such separate formulations may be administered before, after, or simultaneously with the administration of the pravastatin.

The invention is further illustrated by reference to the following examples. It will be apparent to those skilled in the art that many modifications, both to materials and methods, may be practiced without departing from the purpose and scope of the invention.

EXAMPLES

Example 1

Production of Modified Release Pravastatin (Sodium) 10mg Matrix Tablets Using Methocel E4 Premium Modified release formulations of pravastatin, comprising the components set forth in TABLE 1, are produced as follows.

TABLE 1

| Ingredient | FUNCTION | Qty % (w/w) | Qty % (w/w) | Qty % (w/w) |
|---|---|---|---|---|
| PRAVASTATIN (Sodium) | Active | 5.56 | 5.56 | 5.56 |
| LACTOSE ANHYDROUS (DIRECT COMPRESSION GRADE) | Diluent | 58.74 | 53.74 | 48.74 |

TABLE 1-continued

| Ingredient | FUNCTION | Qty % (w/w) | Qty % (w/w) | Qty % (w/w) |
|---|---|---|---|---|
| MICROCRYSTALLINE CELLULOSE (AVICEL PH200) | Dry Binder/diluent | 15.0 | 15.0 | 15.0 |
| METHOCEL E4M PREMIUM CR | Controlled Release Polymer | 20.0 | 25.0 | 30.0 |
| COLLOIDAL SILICON DIOXIDE | Glidant | 0.20 | 0.20 | 0.20 |
| MAGNESIUM STEARATE | Lubricant | 0.50 | 0.50 | 0.50 |
| TOTAL | | 100 | 100 | 100 |

Each ingredient is weighed. The Avicel, pravastatin sodium, colloidal silicon dioxide, methocel, and lactose are mixed in a blender for 15 minutes. The magnesium stearate is added and the ingredients are mixed for a further 5 minutes. The mixture is then divided and compressed into tablets on a suitable tablet machine using plain oval tooling. The target weight of each tablet is 180 mg.

Example 2

Production of Modified Release Pravastatin (Sodium) 10mg Matrix Tablets Using Methocel K100M Premium 2208

The formulations set forth in TABLE 2 are produced according to the process of Example 1.

TABLE 2

| Ingredient | FUNCTION | Qty % (w/w) | Qty % (w/w) | Qty % (w/w) |
|---|---|---|---|---|
| PRAVASTATIN (Sodium) | Active | 5.56 | 5.56 | 5.56 |
| LACTOSE ANHYDROUS (DIRECT COMPRESSION GRADE) | Diluent | 58.74 | 38.74 | 18.74 |
| MICROCRYSTALLINE CELLULOSE (AVICEL PH200) | Dry Binder/diluent | 15.0 | 15.0 | 15.0 |
| METHOCEL K100M PREMIUM CR | Controlled Release Polymer | 20.0 | 40.0 | 60.0 |
| COLLOIDAL SILICON DIOXIDE | Glidant | 0.20 | 0.20 | 0.20 |
| MAGNESIUM STEARATE | Lubricant | 0.50 | 0.50 | 0.50 |
| TOTAL | | 100 | 100 | 100 |

Example 3

Production of Modified Release Pravastatin (Sodium) 10mg Matrix Tablets Using Methocel K100LV Premium The formulations set forth in TABLE 3 are produced according to the process of Example 1.

TABLE 3

| Ingredient | FUNCTION | Qty % (w/w) | Qty % (w/w) | Qty % (w/w) |
|---|---|---|---|---|
| PRAVASTATIN (Sodium) | Active | 5.56 | 5.56 | 5.56 |
| LACTOSE ANHYDROUS (DIRECT COMPRESSION GRADE) | Diluent | 58.74 | 38.74 | 18.74 |

TABLE 3-continued

| Ingredient | FUNCTION | Qty % (w/w) | Qty % (w/w) | Qty % (w/w) |
|---|---|---|---|---|
| MICROCRYSTALLINE CELLULOSE (AVICEL PH200) | Dry Binder/ diluent | 15.0 | 15.0 | 15.0 |
| METHOCEL K100LV PREMIUM CR | Controlled Release Polymer | 20.0 | 40.0 | 60.0 |
| COLLOIDAL SILICON DIOXIDE | Glidant | 0.20 | 0.20 | 0.20 |
| MAGNESIUM STEARATE | Lubricant | 0.50 | 0.50 | 0.50 |
| TOTAL | | 100 | 100 | 100 |

In vitro dissolution tests are performed on the modified release core tablets using the following parameters: USP (711); paddle @ 50 RPM; media: phosphate buffer pH 6.8; and UV absorbance at appropriate wavelength.

Target dissolution is as follows:

| Hour | % Released |
|---|---|
| 1.0 | 10–40 |
| 2.0 | 30–70 |
| 3.0 | ≧45 |
| 4.0 | ≧60 |
| 5.0 | ≧75 |
| 6.0 | ≧80 |

Example 4

Enteric Coated Tablets

Enteric coated matrix tablets are prepared by coating the tablets from Examples 1–3 above with an enteric coating suspension. In order to determine the amount of enteric coating required on the modified release tablets, coating experiments are carried out. The coating trial is carried out on a selected 10 mg strength formulation prototype (Approx. 2–3 kg batch size).

Composition detail for enteric coating suspension:

TABLE 4

| Ingredient | Qty % (w/w) | Qty/Tab (mg) |
|---|---|---|
| *EUDRAGIT L30 D55 (solid content) | 4.0 | TBD |
| TALC, USP | 2.0 | TBD |
| TRIETHYL CITRATE | 0.4 | TBD |
| PURIFIED WATER | 93.6 | N/A |
| TOTAL | 100.0 | |

Manufacturing Process

The coating is applied to the tablets using Eudragit L30 D55, at 5%, 10%, 15%, and 20% of coating polymer thickness (i.e., percentage weight gain on the tablet coat). The coating is applied onto the modified release tablet cores using suitable coating equipment.

In vitro dissolution tests are performed on enteric coated modified release tablets using the following parameters: USP (711); paddle @ 50 RPM; media: 0.01 to 0.1 N HCl for 2 hours, followed by phosphate buffer pH 6.8 or higher for the remainder of the test; UV absorbance at appropriate wavelength.

Samples are collected and subjected to dissolution testing. The target in vitro dissolution for enteric coated tablets is shown below:

| Media | Time point (Hour) | % Released |
|---|---|---|
| Acid | 2.0 | ≦10% |
| pH 6.8 Buffer | 1.0 | 10–40 |
| | 2.0 | 30–70 |
| | 3.0 | ≧45 |
| | 4.0 | ≧60 |
| | 5.0 | ≧75 |
| | 6.0 | ≧80 |

Example 5

Rapid Release Tablet Core

Rapid release tablet cores of pravastatin, comprising the components set forth in TABLE 5, are produced as follows. These cores may be used in membrane-controlled formulations.

TABLE 5

| Ingredient | FUNCTION | Qty % (w/w) | Qty % (w/w) | Qty % (w/w) | Qty % (w/w) | CORE BATCH Qty % (w/w) |
|---|---|---|---|---|---|---|
| PRAVASTATIN (Sodium) | Active | 10.00 | 10.00 | 10.00 | 10.00 | 10.00 |
| LACTOSE ANHYDROUS (DIRECT COMPRESSION GRADE) | Diluent | 79.50 | 67.13 | 44.75 | 22.37 | 79.0 |
| MICROCRYSTALLINE CELLULOSE (AVICEL PH200) | Dry Binder/ diluent | 10.00 | 22.37 | 44.75 | 67.13 | 10.00 |
| MAGNESIUM STEARATE | Lubricant | 0.5 | 0.5 | 0.5 | 0.5 | 1.0 |
| TOTAL | | 100.00 | 100.00 | 100.00 | 100.00 | 100.00 |

Each ingredient is weighed. The Avicel, pravastatin sodium, and lactose are mixed in a blender for 30 minutes. The magnesium stearate is added and the ingredients are mixed for an additional 5 minutes. The mixture is then divided and compressed into tablets on a suitable tablet machine using plain oval tooling. The target weight of each tablet is 180 mg.

A CORE BATCH was prepared using the above method. The results observed for the CORE BATCH were as follows:
Potency (mg/tablet)
minimum: 9.9; maximum: 10.4; mean: 10.1
Tablet Weight
103.7 mg
Tablet Hardness (Newtons)
70 N
Tablet Thickness (mm)
3.8 mm
Disintegration Time (Minutes) (Performed in Distilled Water According to USP Test Method 701)
8 minutes

Example 6

Membrane Coating of Rapid Release Tablets (Membrane Controlled)

The formulations set forth in Example 5 above are coated with the coatings described in TABLE 6.

TABLE 6

| Ingredient | mg/tab) | mg/tab | mg/tab | MEMBRANE CONTROLLED CORE BATCH mg/tab |
|---|---|---|---|---|
| POLYMER | 11.00 | 9.20 | 11.00 | 3.96 |
| SUCROSE | 29.00 | 17.00 | 21.00 | 14.7 |
| ACETYL TRIBUTYL CITRATE | 2.00 | 1.60 | 1.90 | 0.45 |
| CASTOR OIL | 1.00 | 1.2 | 1.4 | 0.34 |
| POLYMERISED SODIUM HYDROGEN CARBONATE | 1.00 | 1.00 | 1.00 | 0.54 |
| ACETONE* | N/A | N/A | N/A | N/A |

Polymer = terpolymer of polyvinyl chloride, polyvinyl acetate, and polyvinyl alcohol (PVC/PVAc/PVOH)
*Solvent is removed during processing.

The dissolution results for the MEMBRANE CONTROLLED CORE BATCH (mean values for six membrane coated core tablets) were as follows, when tested in pH 6.8 buffer; paddle apparatus at 50 RPM:

| Time (hours) | Percent Released |
|---|---|
| 1.0 | 31.1 |
| 2.0 | 61.3 |
| 3.0 | 80.6 |
| 4.0 | 92.3 |
| 5.0 | 97.8 |
| 6.0 | 99.8 |

Example 7

Enteric Coated Membrane Tablets

Enteric coated membrane tablets are prepared by coating the tablets from Example 6 above with an enteric coating suspension. In order to determine the amount of enteric coating required on the modified release tablets, coating experiments are carried out. The coating trial is carried out on a selected 10 mg strength formulation prototype (Approx. 1–2 kg batch size).

Composition detail for enteric coating suspension:

TABLE 7

| Ingredient | Qty % (w/w) | Qty/Tab (mg) |
|---|---|---|
| *EUDRAGIT L30 D55 (solid content) | 4.0 | TBD |
| TALC, USP | 2.0 | TBD |
| TRIETHYL CITRATE | 0.4 | TBD |
| PURIFIED WATER | 93.6 | N/A |
| TOTAL | 100.0 | |

Manufacturing Process

The coating is applied to the membrane coated tablets using Eudragit L30 D55, at 5%, 10%, 15%, and 20% of coating polymer thickness (i.e., percentage weight gain on the tablet coat). The coating is applied onto the membrane coated tablet cores using suitable coating equipment.

In vitro dissolution tests are performed on enteric coated modified release tablets using the following parameters: USP (711); paddle @ 50 RPM; media: 0.01 to 0.1 N HCl for 2 hours, followed by phosphate buffer pH 6.8 or higher for the remainder of the test; UV absorbance at appropriate wavelength.

Samples are collected and subjected to dissolution testing. The target in vitro dissolution for enteric coated tablets is shown below:

| Media | Time point (Hour) | % Released |
|---|---|---|
| Acid | 2.0 | ≦10% |
| pH 6.8 | 1.0 | 10–40 |
| Buffer | 2.0 | 30–70 |
| | 3.0 | ≧45 |
| | 4.0 | ≧60 |
| | 5.0 | ≧75 |
| | 6.0 | ≧80 |

Example 8

Enteric Coated Membrane Tablets

Enteric coated membrane tablets were prepared by coating the MEMBRANE CONTROLLED CORE BATCH tablets from Example 6 above with an enteric coating suspension.

Composition detail for enteric coating suspension:

TABLE 8

| Ingredient | Qty/Tab (mg) |
|---|---|
| EUDRAGIT L100 (solid content) | 6.00 |
| ACETYL TRIBUTYL CITRATE | 1.50 |
| WATER* | N/A |
| ETHANOL* | N/A |
| TOTAL | |

Manufacturing Process

The coating was applied to the membrane coated tablets using Eudragit L100. The coating was applied onto the membrane coated tablet cores using suitable coating equipment.

In vitro dissolution tests were performed on enteric coated modified release tablets using the following parameters: USP (711); paddle @ 50 RPM; media: 0.1 N HCl for 2 hours, followed by phosphate buffer pH 6.8 for the remainder of the test; UV absorbance at appropriate wavelength.

Twelve tablets were collected and subjected to dissolution testing. The mean in vitro dissolution results for the enteric coated tablets is shown below:

| Media | Time point (Hour) | % Released |
|---|---|---|
| Acid (0.1 N HCl) | 1.0 | 0.4 |
|  | 2.0 | 1.7 |
| pH 6.8 Buffer | 1.0 | 30.2 |
|  | 2.0 | 58.4 |
|  | 3.0 | 78.0 |
|  | 4.0 | 90.5 |
|  | 5.0 | 97.6 |
|  | 6.0 | 100.6 |

Example 9 pH-Independent Functional Coating Formulations

Any of the dosage forms according to the present invention may be coated with a pH-independent coating, for example, as provided in TABLE 9 below.

TABLE 9

| Ingredient | FUNCTION | g/Batch |
|---|---|---|
| EUDRAGIT RS 30D | Polymer | 200.00 |
| TALC | Antadherent | 60.00 |
| TRIETHYL CITRATE | Plasticizer | 12.00 |
| SIMETHICONE EMULSION | Dispersant | 1.00 |
| WATER | Solvent | 392.00 |
| TOTAL |  | 665 |

Example 10 pH-Independent Functional Coating Formulations

Any of the dosage forms according to the present invention may be coated with a pH-independent coating, for example, as provided in TABLE 10 below.

TABLE 10

| Ingredient | FUNCTION | g/Batch |
|---|---|---|
| EUDRAGIT RS 12.5 | Polymer | 900 |
| EUDRAGIT RL 12.5 | Polymer | 300 |
| TALC | Antadherent | 105 |
| DIBUTYL SEBECATE | Plasticizer | 15 |
| MAGNESIUM STEARATE | Dispersant | 30 |
| ACETONE | Solvent | 825 |
| ISOPROPYL ALCOHOL | Solvent | 825 |
| TOTAL |  | 3000 |

In vitro dissolution tests are performed on pH-independent functional coated modified release tablets using the following parameters: USP (711); paddle @ 50 RPM; media: phosphate buffer pH 6.8; and UV absorbance at appropriate wavelength.

The target in vitro dissolution for pH-independent functional coated tablets is shown below:

| Media | Time point (Hour) | % Released |
|---|---|---|
| pH 6.8 Buffer | 1.0 | ≦10% |
|  | 2.0 | 10–40% |
|  | 3.0 | 30–70% |
|  | 4.0 | ≧45% |
|  | 5.0 | ≧60% |
|  | 6.0 | ≧75% |
|  | 7.0 | ≧80% |

Example 11

Comparison of Modified Release Pravastatin Formulation and Conventional Pravastatin Formulation in Lowering Cholesterol in a Patient To evaluate the efficacy of the modified release formulations of the present invention, the formulations are tested for reduction of cholesterol in patients with primary hypercholesterolemia and mixed dyslipidemia, and compared to PRAVACHOL® at the same dose. Low doses are also tested to show that the present formulations are more effective at lower doses than PRAVACHOL®. The present formulations are also tested for their effect on systemic ubiquinone depletion relative to the depletion caused by PRAVACHOL®. Results will show that the present formulations cause significantly less systemic ubiquinone depletion relative to conventional formulations of pravastatin, such as PRAVACHOL®.

The study begins with a four-week placebo period, where patients receive dietary advice. Patients are randomized into groups that receive:

A. Conventional pravastatin (PRAVACHOL®) 40 mg daily for 6 weeks; subsequent increase to 80 mg daily for 6 weeks, B. Inventive formulation at 10 mg daily for 6 weeks. At the end of that period, patients are randomized to receive either 10 mg or 20 mg daily for an additional 6 weeks, C. Inventive formulation at 20 mg daily for 6 weeks. At the end of that period, patients are randomized to receive either 20 mg or 40 mg daily for an additional 6 weeks, or D. Inventive formulation at 40 mg for 6 weeks, subsequent increase to 80 mg daily for 6 weeks.

Groups A and D contain 20 patients, while Groups B and C each contain 40 patients, to permit randomization into groups of 20 patients at week 6. This design permits a placebo period, and a dose-response comparison of the present formulations with the conventional product.

Cholesterol levels are measured prior to study entry, prior to randomization (baseline), and at weeks 3, 6, 9, and 12. Systemic ubiquinone levels are measured prior to randomization, and at weeks 6 and 12, to determine the relative depletion of systemic ubiquinone levels. Baseline liver enzymes are measured at weeks 3, 6, 9, and 12. Pravastatin plasma concentrations for population analysis are obtained at weeks 6 and 12.

Efficacy endpoints include the change from baseline in total cholesterol (C), LDL-C, Triglycerides (TG), HDL-C, VLDL-C and the Total-C/HDL-C and LDL-C/HDL-C ratios. Safety will be assessed by considering, among other things, the change from baseline in systemic ubiquinone levels, and the change from baseline in liver transaminase enzymes.

What is claimed is:

1. A method of treating hypercholesterolemia comprising administering, to a subject in need of such treatment, a therapeutically effective amount of pravastatin, or a pharmaceutically acceptable salt thereof, in a pharmaceutical formulation, wherein the formulation inhibits release of the pravastatin in the stomach of the subject, releases a therapeutic amount of pravastatin in the small intestine of the subject over a period of less than 6 hours and achieves a relative systemic bioavailability, as compared to an equally effective dose of a conventional rapid release pravastatin formulation, of less than about 90%.

2. The method of claim 1, wherein the formulation releases greater than about 80% of its pravastatin content in the small intestine.

3. The method of claim 2, wherein the formulation releases greater than 85% of its pravastatin content in the small intestine.

4. The method of claim 2, wherein the formulation release greater than 80% of its pravastatin content in the small intestine over a period of from about 3 hours to less than 6 hours.

5. The method of claim 4, wherein the formulation releases greater than 80% of its pravastatin content in the small intestine over a period of from about 4 hours to about 5 hours.

6. The method according to claim 1, wherein the administration achieves a relative systemic bioavailability, as compared to a conventional rapid release pravastatin formulation, of less than about 80%.

7. The method according to claim 1, wherein the administration achieves a relative Cmax, as compared to a conventional rapid release pravastatin formulation, of less than about 80%.

8. The method according to claim 7, wherein the administration achieves a relative Cmax, as compared to a conventional rapid release pravastatin formulation, of less than about 70%.

9. The method according top claim 1, wherein the formulation is administered to the subject to treat one or more cardiovascular diseases that are secondary to the hypercholesterolemia.

10. The method according to claim 2, wherein the administration reduces the low density lipoprotein-cholesterol (LDL-C) levels in a subject following administration of the formulation.

11. The method according to claim 2, wherein the administration increases high density lipoprotein-cholesterol (HDL-C) levels in a subject following administration of the formulation.

12. The method according to claim 1, wherein said pharmaceutical formulation exhibits a pravastatin release rate, as measured in a Type II dissolution apparatus, in a 0.1N HCl media for 2 hours, followed by pH 6.8 buffer for the remainder of the test of the following:

2 hours, in HCl media: less than or equal to about 20%;
  2 hours, in pH 6.8: greater than or equal to about 20%;
  4 hours, in pH 6.8: greater than or equal to about 40%;
  6 hours, in pH 6.8: greater than or equal to about 60%; and
  12 hours, in pH 6.8: greater than or equal to about 80%.

13. The method according to claim 12, wherein said pharmaceutical formulation exhibits a pravastatin release rate, as measured in a Type II dissolution apparatus, in a 0.1 N HCl media for 2 hours, followed by pH 6.8 buffer for the remainder of the test, of the following:

2 hours, in HCl media: less than or equal to about 20%;
  1 hour, in pH 6.8: 0 to about 50%;
  2 hours, in pH 6.8: about 20% to about 80%;
  4 hours, in pH 6.8: greater than or equal to about 50%;
  6 hours, in pH 6.8: greater than or equal to about 70%;
  12 hours, in pH 6.8: greater than or equal to about 80%.

14. The method according to claim 12, wherein said pharmaceutical formulation exhibits a pravastatin release rate, as measured in a Type II dissolution apparatus, in a 0.1 N HCl media for 2 hours, followed by pH 6.8 buffer for the remainder of the test, of the following:

2 hours, in HCl media: less than or equal to about 10%;
  1 hour, in pH 6.8: about 10 to about 40%;
  2 hours, in pH 6.8: about 30% to about 70%;
  3 hours, in pH 6.8: greater than or equal to about 45%;
  4 hours, in pH 6.8: greater than or equal to about 60%;
  5 hours, in pH 6.8: greater than or equal to about 75%; and
  6 hours, in pH 6.8: greater than or equal to about 80%.

15. The method according to claim 14, wherein said pharmaceutical formulation exhibits a pravastatin release rate, as measured in a Type II dissolution apparatus, in a 0.1 N HCl media for 2 hours, followed by pH 6.8 buffer for the remainder of the test, of the following:

2 hours, in HCl media: less than or equal to about 5%;
  1 hour, in pH 6.8: about 10 to about 40%;
  2 hours, in pH 6.8: about 30% to about 70%;
  3 hours, in pH 6.8: greater than or equal to about 45%;
  4 hours, in pH 6.8: greater than or equal to about 60%; and
  5 hours, in pH 6.8: greater than or equal to about 80%.

16. The method according to claim 15, wherein said pharmaceutical formulation exhibits a pravastatin release rate, as measured in a Type II dissolution apparatus, in a pH 6.8 buffer, of the following:

2 hours, in pH 6.8: greater than or equal to about 20%;
  4 hours, in pH 6.8: greater than or equal to about 40%;
  6 hours, in pH 6.8: greater than or equal to about 60%; and
  12 hours, in pH 6.8: greater than or equal to about 80%.

17. The method according to claim 16, wherein said pharmaceutical formulation exhibits a pravastatin release rate, as measured in a Type II dissolution apparatus, in a pH 6.8 buffer, of the following:

1 hour, in pH 6.8: 0 to about 50%;
  2 hours, in pH 6.8: about 20% to about 80%;
  4 hours, in pH 6.8: greater than or equal to about 50%;
  6 hours, in pH 6.8: greater than or equal to about 70%;
  12 hours, in pH 6.8: greater than or equal to about 80%.

18. The method according to claim 17, wherein said pharmaceutical formulation exhibits a pravastatin release rate, as measured in a Type II dissolution apparatus, in a pH 6.8 buffer, of the following:

1 hour, in pH 6.8: about 10 to about 40%;
  2 hours, in pH 6.8: about 30% to about 70%;
  3 hours, in pH 6.8: greater than or equal to about 45%;
  4 hours, in pH 6.8: greater than or equal to about 60%;
  5 hours, in pH 6.8: greater than or equal to about 75%; and
  6 hours, in pH 6.8: greater than or equal to about 80%.

19. The method according to claim 18, wherein said pharmaceutical formulation exhibits a pravastatin release rate, as measured in a Type II dissolution apparatus, in a pH 6.8 buffer, of the following:

1 hour, in pH 6.8: about 10 to about 40%;
2 hours, in pH 6.8: about 30% to about 70%;
3 hours, in pH 6.8: greater than or equal to about 45%;
4 hours, in pH 6.8: greater than or equal to about 60%; and
5 hours, in pH 6.8: greater than or equal to about 80%.

20. A modified-release pravastatin formulation comprising pravastatin, or a pharmaceutically acceptable salt thereof, and a pH-independent coating, which formulation exhibits a pravastatin release rate, as measured in a Type II dissolution apparatus, in a pH 6.8 buffer, of the following:

1 hour, in pH 6.8: less than or equal to about 20%;
3 hours, in pH 6.8: greater than or equal to about 20%;
5 hours, in pH 6.8: greater than or equal to about 40%;
7 hours, in pH 6.8: greater than or equal to about 60%; and
12 hours, in pH 6.8: greater than or equal to about 80%.

21. The modified-release pravastatin formulation according to claim 20, which exhibits a pravastatin release rate, as measured in a Type II dissolution apparatus, in a pH 6.8 buffer, of the following:

1 hour, in pH 6.8: less than or equal to about 20%;
2 hours, in pH 6.8: about 20 to about 80%;
5 hours, in pH 6.8: greater than or equal to about 50%;
7 hours, in pH 6.8: greater than or equal to about 70%; and
12 hours, in pH 6.8: greater than or equal to about 80%.

22. The modified-release pravastatin formulation according to claim 21, which exhibits a pravastatin release rate, as measured in a Type II dissolution apparatus, in a pH 6.8 buffer, of the following:

1 hour, in pH 6.8: less than or equal to about 10%;
2 hours, in pH 6.8: about 10 to about 40%;
3 hours, in pH 6.8: about 30 to about 70%;
4 hours, in pH 6.8: greater than or equal to about 45%;
5 hours, in pH 6.8: greater than or equal to about 60%;
6 hours, in pH 6.8: greater than or equal to about 75%; and
7 hours, in pH 6.8: greater than or equal to about 80%.

23. The modified-release pravastatin formulation according to claim 22, which exhibits a pravastatin release rate, as measured in a Type II dissolution apparatus, in a pH 6.8 buffer, of the following:

1 hour, in pH 6.8: less than or equal to about 5%;
2 hours, in pH 6.8: about 10 to about 40%;
3 hours, in pH 6.8: about 30 to about 70%;
4 hours, in pH 6.8: greater than or equal to about 45%;
5 hours, in pH 6.8: greater than or equal to about 60%; and
6 hours, in pH 6.8: greater than or equal to about 80%.

24. A method for treating one or more cardiovascular diseases that are not secondary to hypercholesterolemia comprising administering, to a subject in need of such treatment, a therapeutically effective amount of pravastatin, or a pharmaceutically acceptable salt thereof, in a pharmaceutical formulation, and releases a therapeutic amount of pravastatin in the small intestine of the subject over a period of less than 6 hours, and achieves a relative systemic bioavailability, as compared to an equally effective dose of a conventional rapid release pravastatin formulation, of less than about 90%.

25. A method for increasing the hepatic availability of pravastatin comprising administering to a subject a therapeutically effective amount of pravastatin, or a pharmaceutically acceptable salt thereof, in a non-enteric coated pharmaceutical formulation exhibiting a pravastatin release rate, as measured in a Type II dissolution apparatus, in a 0.1N HCl media for 2 hours, followed by pH 6.8 buffer for the remainder of the test, of the following:

2 hours, in HCl media: less than or equal to about 10%;
1 hour, in pH 6.8: about 10 to about 40%;
2 hours, in pH 6.8: about 30% to about 70%;
3 hours, in pH 6.8: greater than or equal to about 45%;
4 hours, in pH 6.8: greater than or equal to about 60%;
5 hours, in pH 6.8: greater than or equal to about 75%; and
6 hours, in pH 6.8: greater than or equal to about 80%.

26. The formulation of claim 25, wherein the therapeutically effective amount of pravastatin ranged from about 1 to about 200 mg.

27. The formulation of claim 26, wherein the therapeutically effective amount of pravastatin ranged from about 5 to about 80 mg.

28. A method for increasing the hepatic availability of pravastatin comprising administering to a subject a therapeutically effective amount of pravastatin, or a pharmaceutically acceptable salt thereof, in a non-enteric coated pharmaceutical formulation exhibiting a pravastatin release rate, as measured in a Type II dissolution apparatus, in a pH 6.8 buffer, of the following:

1 hour, in pH 6.8: less than or equal to about 10%;
2 hours, in pH 6.8: about 10 to about 40%;
3 hours, in pH 6.8: about 30 to about 70%;
4 hours, in pH 6.8: greater than or equal to about 45%;
5 hours, in pH 6.8: greater than or equal to about 60%;
6 hours, in pH 6.8: greater than or equal to about 75%; and
7 hours, in pH 6.8: greater than or equal to about 80%.

29. The formulation of claim 28, wherein the therapeutically effective amount of pravastatin ranges from about 1 to about 200 mg.

30. The formulation of claim 29, wherein the therapeutically effective amount of pravastatin ranges from about 5 to about 80 mg.

31. A method of reducing one or more side effects associated with the administration of pravastatin, comprising administering a therapeutically effective amount of pravastatin, or a pharmaceutically acceptable salt thereof, in a pharmaceutical formulation to a subject in need of such reduction in side effects, wherein the formulation inhibits release of the pravastatin in the stomach of the subject, releases a therapeutic amount of pravastatin in the small intestine of the subject over a period of less than 6 hours, achieves a relative systemic bioavailability, as compared to an equally effective dose of a conventional rapid release formulation, of less than about 90%, and wherein one or more side-effects are reduced relative to those resulting from the administration of an equivalent amount of a conventional rapid release formulation of pravastatin.

32. The method according to claim 31, wherein the formulation exhibits a pravastatin release rate, as measured in a Type II dissolution apparatus, in a 0.1N HCl media for 2 hours, followed by a pH 6.8 buffer for the remainder of the test, of the following:

2 hours, in HCl media: less than or equal to about 10%;
1 hour, in pH 6.8: about 10 to about 40%;
2 hours, in pH 6.8: about 30% to about 70%;
3 hours, in pH 6.8: greater than or equal to about 45%;
4 hours, in pH 6.8: greater than or equal to about 60%;
5 hours, in pH 6.8: greater than or equal to about 75%; and
6 hours, in pH 6.8: greater than or equal to about 80%.

33. The method according to claim 31, wherein the formulation exhibits a pravastatin release rate, as measured in a Type II dissolution apparatus, in a pH 6.8 buffer, of the following:

1 hour, in pH 6.8: less than or equal to about 10%;
2 hours, in pH 6.8: about 10% to about 40%;
3 hours, in pH 6.8: about 30 to about 70%;
4 hours, in pH 6.8: greater than or equal to about 45%;
5 hours, in pH 6.8: greater than or equal to about 60%;
6 hours, in pH 6.8: greater than or equal to about 75%; and
7 hours, in pH 6.8: greater than or equal to about 80%.

34. A method of reducing one or more drug interactions associated with administration of conventional rapid release pravastatin formulations comprising administering a therapeutically effective amount of pravastatin, or a pharmaceutically acceptable salt thereof, to a subject in need of such a reduction, wherein one or more drug interactions are reduced relative to those resulting from the administration of an equivalent amount of pravastatin from a conventional rapid release pravastatin formulational;

and wherein the pravastatin is administered in a fomulation that inhibits release of the pravastatin in the stomach of the subject over a period of less than 6 hours, achieves a relative systemic bioavailability, as compared to an equally effective dose of a convention rapid release pravastatin formulation, of less than about 90%.

35. A method of reducing one or more side effects associated with the administration of pravastatin, or associated with the co-administration of pravastatin with other lipid lowering drugs, comprising:

administering a therapeutically effective amount of pravastatin, or a pharmaceutically acceptable salt thereof, in a pharmaceutical formulation to a subject in need of such reduction in side effects, in combination with a different lipid-lowering drug chosen from HMG-CoA reductase inhibitors, fibrates, modifiers of cholesterol absorption, and bile acid-binding resins, wherein the formulation inhibits release of the pravastatin in the stomach of the subject over a period of less than 6 hours, achieves a relative systemic bioavailability, as compared to an equally effective dose of a conventional rapid release pravastatin formulation, of less than about 90%, and wherein one or more side-effects are reduced relative to those resulting from co-administration of an equivalent amount of a conventional rapid release formulation of pravastatin and said lipid-lowering drug.

36. The method of claim 1, wherein the therapeutically effective amount of pravastatin ranges from about 1 to about 200 mg.

37. The method of claim 36, wherein the therapeutically effective amount of pravastatin ranges from about 5 to about 80 mg.

38. The method of claim 12, wherein the formulation comprises an amount of pravastatin ranging from about 1 to about 200 mg.

39. The method of claim 38, wherein the formulation comprises an amount of pravastatin ranging from about 5 to about 80 mg.

40. The method of claim 16, wherein the formulation comprises an amount of pravastatin ranging from about 1 to about 200 mg.

41. The method of claim 40, wherein the formulation comprises an amount of pravastatin ranging from about 5 to about 80 mg.

42. The formulation of claim 20, wherein the therapeutically effective amount of pravastatin ranges from about 1 to about 200 mg.

43. The formulation of claim 42, wherein the therapeutically effective amount of pravastatin ranges from about 5 to about 80 mg.

44. The method of claim 31, wherein the therapeutically effective amount of pravastatin ranges from about 1 to about 200 mg.

45. The method of claims 44, wherein the therapeutically effective amount of pravastatin ranges from about 5 to about 80 mg.

46. A method of treating hypercholesterolemia comprising administering, to a subject in need of such treatment, a therapeutically effective amount of pravastatin, or a pharmaceutically acceptable salt thereof, in a non-enteric coated phannaceutical formulation, wherein the formulation inhibits release of the pravastatin in the stomach of the subject, and releases a therapeutic amount of pravastatin in the small intestine of the subject over a period of less than 6 hours.

47. The method of claim 46, wherein the formulation releases greater than about 80% of its pravastatin content in the small intestine.

48. The method of claim 47, wherein the formulation releases greater than 85% of its pravastatin content in the small intestine.

49. The method of claim 47, wherein the formulation release greater than 80% of its pravastatin content in the small intestine over a period of from about 3 hours to less than 6 hours.

50. The method of claim 49, wherein the formulation releases greater than 80% of its pravastatin content in the small intestine over a period of from about 4 hours to about 5 hours.

51. The method of claim 46, wherein the administration achieves a relative systemic bioavailability, as compared to a conventional rapid release pravastatin formulation, of less than about 90%.

52. The method according to claim 51, wherein the administration achieves a relative systemic bioavailability, as compared to a conventional rapid release pravastatin formulation, of less than about 80%.

53. The method according to claim 46, wherein the administration achieves a relative Cmax, as compared to a conventional rapid release pravastatin formulation, of less than about 80%.

54. The method according to claim 53, wherein the administration achieves a relative Cmax, as compared to a conventional rapid release pravastatin formulation, of less than about 70%.

55. The method according top claim 46, wherein the formulation is administered to the subject to treat one or more cardiovascular diseases that are secondary to the hypercholesterolemia.

56. The method according to claim 46, wherein the administration reduces the low density lipoprotein-cholesterol (LDL-C) levels in a subject following administration of the formulation.

57. The method according to claim 47, wherein the administration increases high density lipoprotein-cholesterol (HDL-C) levels in a subject following administration of the formulation.

* * * * *